(12) United States Patent
Kane et al.

(10) Patent No.: US 11,534,219 B2
(45) Date of Patent: Dec. 27, 2022

(54) HYBRID RADIOLUCENT SCREW WITH RADIOPAQUE COMPONENTS AND RADIOLUCENT COMPONENTS AND METHOD OF MANUFACTURE

(71) Applicant: ESP Medical Solutions, LLC, Gladwyne, PA (US)

(72) Inventors: Patrick M. Kane, Gladwyne, PA (US); Eon K. Shin, Gladwyne, PA (US); Sidney Jacoby, Gladwyne, PA (US)

(73) Assignee: ESP Medical Solutions, LLC, Gladwyne, PA (US)

( * ) Notice: Subject to any disclaimer, the term of this patent is extended or adjusted under 35 U.S.C. 154(b) by 554 days.

(21) Appl. No.: 15/819,099

(22) Filed: Nov. 21, 2017

(65) Prior Publication Data

US 2019/0151000 A1 May 23, 2019

(51) Int. Cl.

| | | |
|---|---|---|
| *A61B 17/86* | (2006.01) |
| *A61L 31/18* | (2006.01) |
| *A61L 31/06* | (2006.01) |
| *A61L 31/14* | (2006.01) |
| A61B 17/00 | (2006.01) |
| A61B 90/00 | (2016.01) |

(52) U.S. Cl.
CPC ......... *A61B 17/866* (2013.01); *A61B 17/863* (2013.01); *A61B 17/8615* (2013.01); *A61B 17/8635* (2013.01); *A61L 31/06* (2013.01); *A61L 31/14* (2013.01); *A61L 31/18* (2013.01); A61B 17/864 (2013.01); A61B 2017/0092 (2013.01); A61B 2017/00526 (2013.01); A61B 2017/00955 (2013.01); A61B 2090/3966 (2016.02)

(58) Field of Classification Search
CPC .............. A61B 17/8615; A61B 17/863; A61B 17/8635; A61B 17/866; A61B 2017/8655
See application file for complete search history.

(56) References Cited

U.S. PATENT DOCUMENTS

| | | | | |
|---|---|---|---|---|
| 4,175,555 A | * | 11/1979 | Herbert | F16B 5/0275 606/304 |
| 5,827,285 A | * | 10/1998 | Bramlet | A61B 17/68 606/60 |
| 6,458,134 B1 | * | 10/2002 | Songer | A61B 17/68 606/304 |
| 7,582,107 B2 | | 9/2009 | Trail et al. | |
| 7,601,172 B2 | * | 10/2009 | Segal | A61F 2/441 623/17.11 |
| 9,408,649 B2 | * | 8/2016 | Felix | A61B 17/7037 |
| 9,861,413 B2 | * | 1/2018 | Palmer | A61B 17/8894 |
| 10,092,339 B2 | * | 10/2018 | Biedermann | A61B 17/8685 |
| 10,194,950 B2 | * | 2/2019 | Felix | A61B 17/7032 |
| 2010/0063550 A1 | | 3/2010 | Felix et al. | |
| 2011/0172718 A1 | * | 7/2011 | Felix | A61B 17/7032 606/305 |
| 2011/0257689 A1 | | 10/2011 | Fiechter et al. | |
| 2014/0188180 A1 | | 7/2014 | Biedermann et al. | |

* cited by examiner

*Primary Examiner* — Anu Ramana

(74) *Attorney, Agent, or Firm* — Polsinelli PC; Adam Rehm

(57) ABSTRACT

A hybrid radiolucent screw having radiopaque components and radiolucent components, which collaboratively define a tip of the screw and a head of the screw. In this manner, distortion is minimized during fluoroscopy or radiography of the screw while visualization of the screw and surrounding area is enhanced.

19 Claims, 3 Drawing Sheets

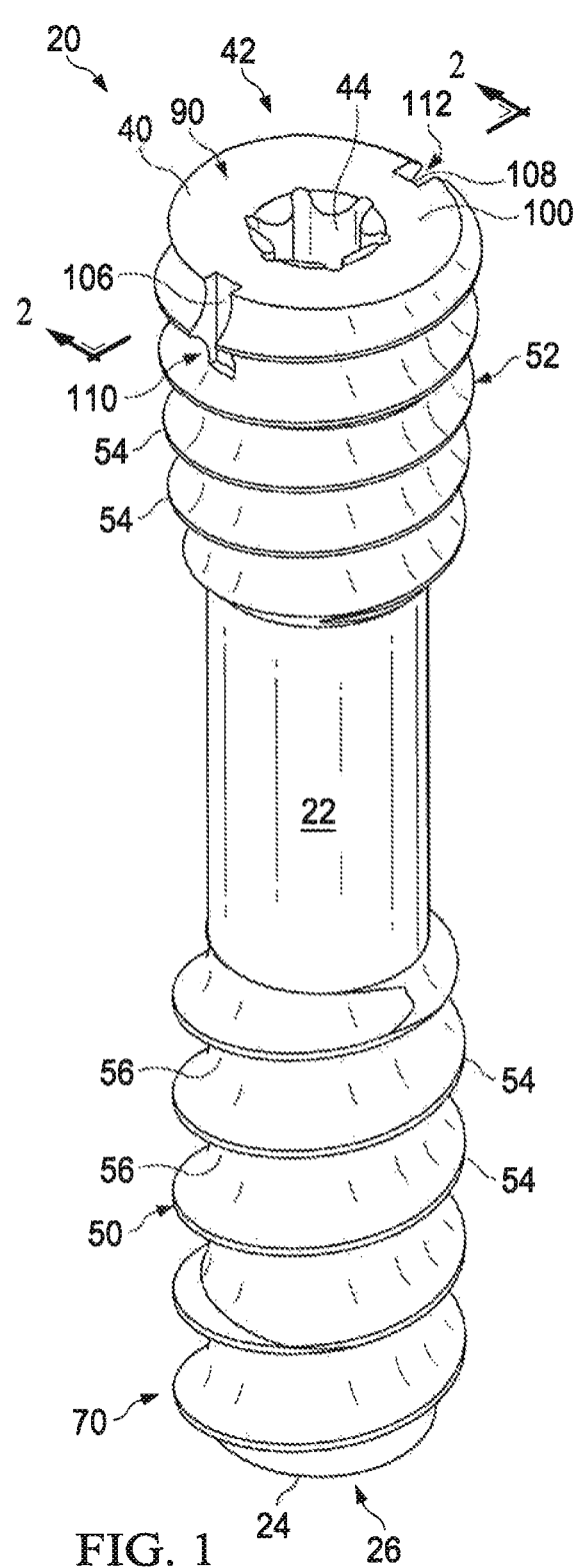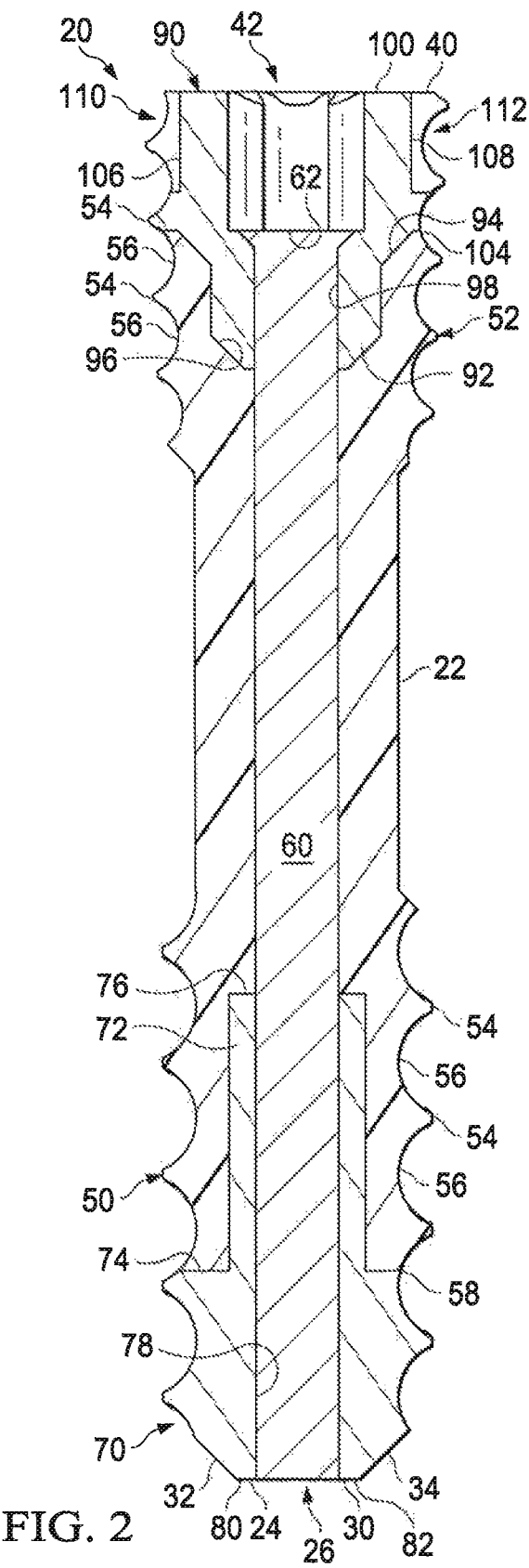
FIG. 1
FIG. 2

HYBRID RADIOLUCENT SCREW WITH RADIOPAQUE COMPONENTS AND RADIOLUCENT COMPONENTS AND METHOD OF MANUFACTURE

BACKGROUND OF THE INVENTION

1. Field of the Invention

The present inventive concept relates generally to medical screws, and more particularly, to a hybrid radiolucent screw with radiopaque components and radiolucent components.

2. Description of the Related Art

Many conventional implants, e.g., surgical plates and surgical screws, are made of a metal alloy, e.g., titanium or stainless steel. After installation of a conventional implant, the alloy causes the implant to obscure views of areas adjacent to and surrounding the implant on an X-ray image and distort the areas. This distortion is problematic because, for among other reasons, such prevents a surgeon from evaluating whether the implant has been properly placed and otherwise assessing the areas adjacent to and surrounding the implant. For instance, when the implant has been utilized for fracture fixation, it might be desirable to assess the fracture site to ensure proper fracture healing.

Attempts to remedy this problem include use of radiolucent material. Such conventional implants, however, suffer from various limitations. For instance, U.S. Pat. No. 7,998,180 to Erickson, which is incorporated herein by reference in its entirety, provides a radiolucent screw for use in spinal fusion with radiopaque markers. When the Erickson screw is being installed in a patient during a surgical procedure, however, it is common for the screw to break given low torque properties of the Erickson screw. Such breakage results in increased costs and can be lethal as such lengthens the time period required of the surgical procedure, which increases trauma to the patient thus extending recover time of the patient from the surgical procedure, elevates risks associated with the surgical procedure, and increases the costs of the surgical procedure.

Accordingly, there is a need for screw that does not suffer from the limitations of conventional implants, provides enhanced visibility with minimized distortion, enhances safety during use thereof, has a simple design that is easy to use, and does not prolong recovery time or expenses of a patient.

SUMMARY OF THE INVENTION

The following brief description is provided to indicate the nature of the subject matter disclosed herein. While certain aspects of the present inventive concept are described below, the summary is not intended to limit the scope of the present inventive concept. Embodiments of the present inventive concept provide an inventive concept for a hybrid radiolucent screw having radiopaque components and radiolucent components. In this manner, distortion is minimized during fluoroscopy or radiography of the screw, thereby enhancing visualization of the screw and surrounding areas. Also provided is a method of manufacturing the screw. The present inventive concept does not suffer from and remedies the deficiencies of conventional screws such as those previously set forth herein.

The present inventive concept provides, in its simplest form, a hybrid radiolucent screw having radiopaque components and radiolucent components, which are secured together, e.g., via bonding, to collaboratively form a tip of the screw, a head of the screw, and multiple sets of threads. The screw may be one or more of a plurality of designs to provide one or more of a plurality of functions. The screw includes design elements, which provide increased functionality relative to conventional screws.

An object of the present inventive concept is to provide a screw that allows for improved fluoroscopic and radiographic visualization by minimizing distortion and obfuscation caused by metallic artifact with fluoroscopy and radiography. The improved fluoroscopic and radiographic visualization advantageously allows for implantation or placement of the screw of the present inventive concept with increased accuracy, and enhanced visualization and assessment of fracture healing and/or bone fusion. The improved fluoroscopic and radiographic visualization provided by the present inventive concept can be utilized with traditional as well as advanced imaging studies, e.g., computed tomography or magnetic resonance imaging.

Another object of the present inventive concept is to advantageously provide a surgeon with complete awareness of screw positioning and alignment by providing radiopaque components at ends of the screw, i.e., a head and a tip.

Another object of the present inventive concept is to advantageously minimize distortion that occurs with advanced imaging, such as CT or MRI studies, where metallic implants will cause distortion of the images and significantly impair a physician's ability to assess fracture healing by using radiolucent materials such as PEEK, which is completely transparent with radiography.

Another object of the present inventive concept is to advantageously provide enhanced cutting and tapping qualities by providing a metallic component at the tip of the screw, thereby facilitating implantation or placement of the screw.

Another object of the present inventive concept is to advantageously provide increased torque cutting by providing a metallic component at the head of the screw, thereby enhancing compression of the screw to facilitate implantation or placement of the screw while preventing stripping of the screw.

Another object of the present inventive concept is to advantageously minimize effects of stress shielding while improving bone healing potential by utilize a radiolucent material, e.g., polyether ether ketone (PEEK), with a modulus of elasticity similar to cortical bone.

Another object of the general inventive concept is to provide a screw that is easy to use, comparatively simple to manufacture, and especially well adapted for the intended usage thereof.

Another object of the general inventive concept is to provide a screw that can be used in conjunction with a plating system or as a stand-alone bony fixation construct.

Another object of the general inventive concept is to provide a screw that can incorporate biologic substrates to augment bony fixation and fusion and to minimize infections and other post-operative complications. Examples of possible biologic substrates include, but are not limited to, hydroxyapatite, calcium sulfate, calcium phosphate, and/or antibiotic coatings.

The aforementioned objects and advantages of the present inventive concept may be achieved by providing a screw. The screw may include an elongated body. The screw may further include a tip (i) at a first end of the body, and/or (ii) at least partially defined by a first component and a second component. The screw may further include a head (i) at a second end of the body, (ii) at least partially defined by at least one of the first component and a third component, and/or (iii) having a central receiver formed at least partially therein. The screw may further include a first set of threads at least partially defined by at least one of the second component and the body. The screw may further include a second set of threads at least partially defined by at least one of the third component and the body.

The tip may be defined by the first component and/or the second component. The second component may include an interior abutment surface spaced from an exterior abutment surface. The second component may abut the body at the interior abutment surface and/or the exterior abutment surface. The second component may abut the body along the first set of threads, and/or within outermost perimeters of the first set of threads. The first set of threads may be defined by the second component and the body. The head may be defined by the first component, the body, and/or the third component.

The third component may include an interior abutment surface and/or an exterior abutment surface. The third component may abut the body at the interior abutment surface and/or the exterior abutment surface. The third component may abut the body along the first set of threads. The second set of threads may be defined by the body and/or the third component.

The screw may further include an elongated receiver formed in the second set of threads. The elongated receiver may expose at least a portion of the third component.

The body may be formed of a radiolucent material. The first component may be formed of a radiopaque material and/or the radiolucent material. The second component and the third component may be formed of the radiopaque material and/or the radiolucent material. Only a portion of the tip may be formed of polyether ether ketone.

The aforementioned objects and advantages of the present inventive concept may further be achieved by providing a method of manufacturing a hybrid screw. The method may include the step of forming an elongated radiolucent body, which may define at least a portion of a first set of threads and at least a portion of a second set of threads. The method may also include the step of extending a core into the body. The core may be radiopaque, radiolucent, or a combination thereof. The method may also include the step of securing a first radiopaque component to the core and/or abutting the body. The core and/or the first radiopaque component may form a tip of the screw. The method may also include the step of securing a second radiopaque component to the core and/or abutting the body. The body and/or the second radiopaque component may form at least a portion of a head of the screw.

The first radiopaque component may include an interior abutment surface spaced from an exterior abutment surface, and/or abut the body at the interior abutment surface and/or the exterior abutment surface. The first radiopaque component may abut the body along the first set of threads and/or within outermost perimeters of the first set of threads. The first set of threads may be defined by the first radiopaque component and/or the body. The head may be defined by the core, the body, and/or the second radiopaque component.

The second radiopaque component includes an interior abutment surface and an exterior abutment surface, and/or abuts the body at the interior abutment surface and the exterior abutment surface. The second radiopaque component may abut the body along the first set of threads. The second set of threads may be defined by the body and the second radiopaque component.

The foregoing and other objects are intended to be illustrative of the present inventive concept and are not meant in a limiting sense. Many possible embodiments of the present inventive concept may be made and will be readily evident upon a study of the following specification and accompanying drawings comprising a part thereof. Various features and subcombinations of present inventive concept may be employed without reference to other features and subcombinations. Other objects and advantages of this present inventive concept will become apparent from the following description taken in connection with the accompanying drawings, wherein is set forth by way of illustration and example, an embodiment of this present inventive concept and various features thereof.

BRIEF DESCRIPTION OF THE DRAWINGS

A preferred embodiment of the present inventive concept, illustrative of the best mode in which the applicant has contemplated applying the principles, is set forth in the following description and is shown in the drawings.

FIG. 1 is a perspective view of a hybrid radiolucent screw of the present inventive concept prior before implanting the screw in a patient by a surgeon during an orthopedic surgical procedure;

FIG. 2 is cross-section view of the screw of FIG. 1 taken along line 2-2 of FIG. 1;

DETAILED DESCRIPTION

Figure 3:
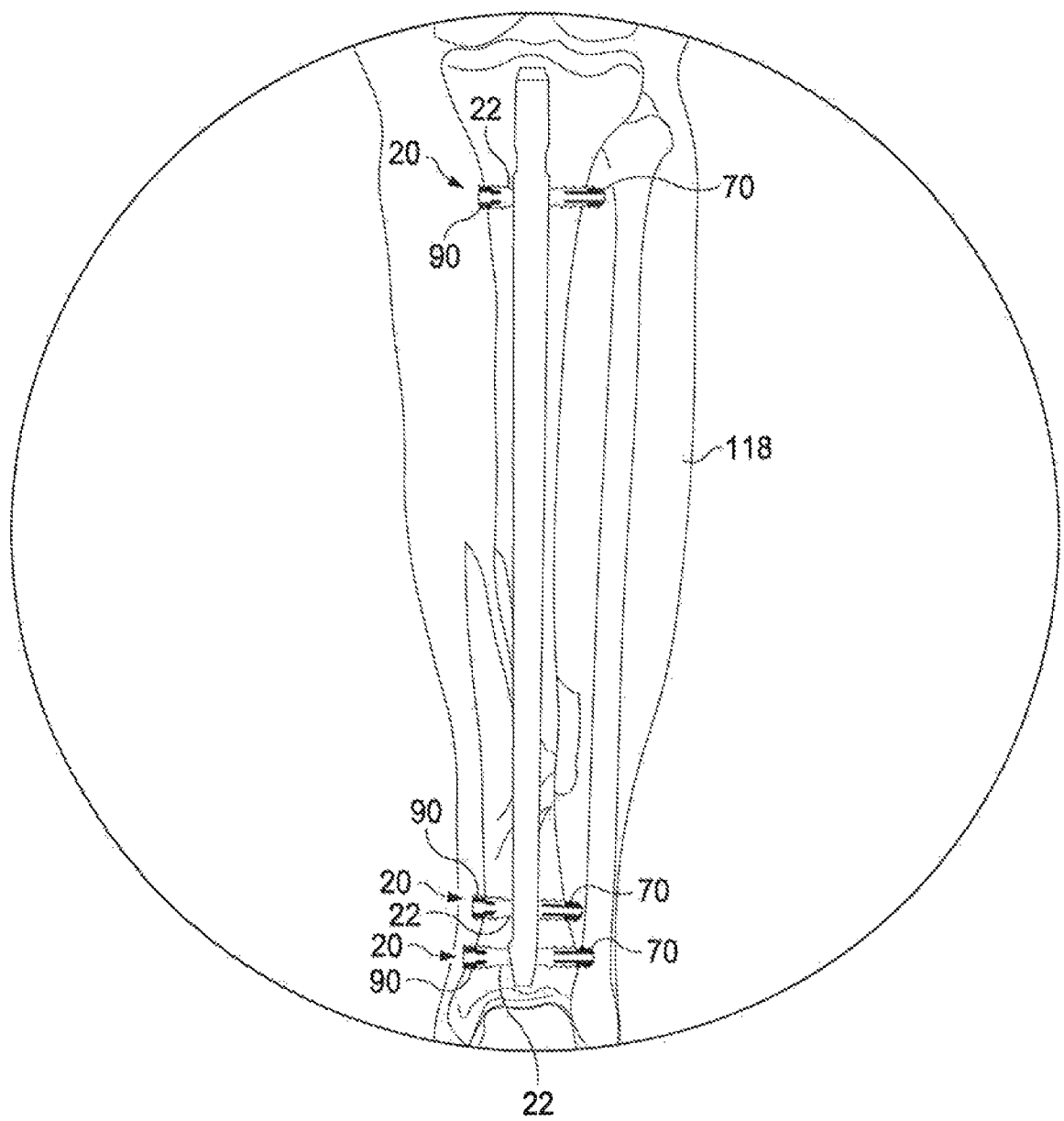
FIG. 3 is an X-ray image of the screw illustrated in FIG. 1, after implanting the screw in the patient, showing radiopaque components of the screw having enhanced visibility, and a radiolucent core and a radiolucent body being significantly less visible than the radiopaque components and nearly invisible.

The following detailed description of the present inventive concept references the accompanying drawings that illustrate specific embodiments in which the present inventive concept can be practiced. The embodiments are intended to describe aspects of the present inventive concept in sufficient detail to enable those skilled in the art to practice the present inventive concept. Other embodiments can be utilized and changes can be made without departing from the scope of the present inventive concept. The following detailed description is, therefore, not to be taken in a limiting sense. The scope of the present inventive concept is defined only by the appended claims, along with the full scope of equivalents to which such claims are entitled.

In this description, references to "embodiment" or "embodiments" mean that the feature or features being referred to are included in at least one embodiment of the technology. Separate references to "embodiment" or "embodiments" in this description do not necessarily refer to the same embodiment and are also not mutually exclusive unless so stated and/or except as will be readily apparent to those skilled in the art from the description. For example, a feature, structure, act, or the like described in one embodiment may also be included in other embodiments, but is not necessarily included. Thus, the present technology can include a variety of combinations and/or integrations of the embodiments described herein.

Turning to the drawings and particularly FIGS. 1 and 2, a screw 20 of the present inventive concept is illustrated prior to use by a surgeon during an orthopedic surgical procedure. The screw 20 includes an elongated body 22, which is formed along an elongated, central axis of the screw 20. The body 22 is formed of a radiolucent material with a modulus of elasticity that is the same as or substantially similar to that of cortical bone. In the exemplary embodiment, the body 22 is formed of a thermoplastic polymer such as polyether ether ketone (PEEK), but it is foreseen that the body 22 may be formed of another material with same or similar properties without deviating from the scope of the present inventive concept. For instance, it is foreseen that any radiolucent portion of the screw 20 may be made of carbon, fiberglass, poly paraphenylene terephthalamide (PPTA), which is also known via the federal trademark KEVLAR®, other aramids, or ceramics without deviating from the scope of the present inventive concept. It is foreseen that any radiolucent portion of the screw 20 may be made of radiolucent, biocompatible fibers having similar properties without deviating from the scope of the present inventive concept. Examples of thermoplastic materials that can be used include polyester, vinylester, polycarbonate, polyetheretherketone (PEEK), polyaryletherketone (PAEK), polyethylene, polyurethane, and polyamide. Examples of thermoset materials that can be used include epoxies and polyimides. Exemplary biocompatible epoxies include the Master Bond Inc. epoxies EP42HT-2 and EP45HT MED and the Epotek epoxies 301-2 and 375. Examples of ceramics that can be used include alumina and zirconia. Other epoxies, ceramics, plastics and resins that are implantable, biocompatible, sterilizable, and have the desired strength properties can also be used without deviating from the scope of the present inventive concept. It is also foreseen that one or more portions of the screw 20 may be formed of a non-degradable material such as, but not limited to, PEEK or biodegradable material such as, but not limited to, PLLAa poly-1-lactide acid (PLLA) without deviating from the scope of the present inventive concept.

The screw 20 further includes a tip 24, which defines an outermost surface of a first end 26 of the screw 20. In the exemplary embodiment, the first end 26 of the screw 20 includes a plateau 30 between angled sides 32, 34. It is foreseen, however, that the first end 26 could be formed without the plateau 30 so that the sides 32, 34 meet at a common point without deviating from the scope of the present inventive concept.

The screw 20 further includes a head 40, which defines an outermost surface of a second end 42 of the screw 20. In the exemplary embodiment, the head 40 includes a nested receiver 44 formed therein and extending partially into a centermost portion of the head 40 and along the central axis of the body 22.

The screw 20 further includes a first set of threads 50 and a second set of threads 52, which are spaced from each other along the body 22. The first set of threads 50 begin at the first end 26 and adjacent to the tip 24, and partially extend along the body 22. The second set of threads 52 begin and partially extend along the body 22 and terminate at the second end 42 and adjacent to the head 40. Each of the threads 50, 52 include a plurality of alternating crests 54 and roots 56, with sloped surfaces therebetween. The plurality of crests 54 define a major diameter of the threads 50, 52, the plurality of roots 56 define a minor diameter of the threads 50, 52, and each sloped surface of the sloped surfaces therebetween define a thread angle of the threads 50, 52.

A first component or core 60 extends entirely between the first end 26 and the second end 42, and along the central axis of the body 22. In the exemplary embodiment, an outermost portion of the core 60 forms a portion of the plateau 30 at the first end 26, and defines at least a portion of the receiver 44, i.e., forms an interior bottom surface 62, at the second end 42 of the screw 20. In the exemplary embodiment, the core 60 has a uniform diameter from the plateau 30 to a point adjacent to the receiver 44, at which point the diameter progressively increases and terminates at the bottom surface 62 of the receiver 44. The core 60 may be formed of a radiolucent material, a radiopaque material, or a combination thereof without deviating from the scope of the present inventive concept. In the exemplary embodiment, the core 60 is formed of a material having a modulus of elasticity that is the same as or substantially similar to that of cortical bone, such as, but not limited to thermoplastic polymer, e.g., polyether ether ketone (PEEK) and/or other radiolucent material including, but not limited to the other radiolucent materials disclosed herein. It is foreseen, however, that the core 60 may be formed of a radiopaque material such as, but not limited to metal or the like, without deviating from the scope of the present inventive concept.

A second component or tip insert 70 includes an extension 72 that extends partially into the body 22 from an exterior abutment surface 74 of the tip insert 70. The tip insert 70 abuts the body at the exterior abutment surface 74 and at an interior abutment surface 76 of the tip insert 70, which is spaced from the exterior abutment surface 74 and forms an end of the extension 72 of the tip insert 70. An aperture 78 extends along an entire length of the tip insert 70 and receives a portion of the core 60 therethrough. In this manner, outermost planar portions 80, 82 of the tip insert 70, and the core 60 collectively form the plateau 30, and outermost angled portions of the tip insert 70 form the angled sides 32, 34. The tip insert 70 forms a portion of the first set of threads 50 with a remainder portion of the first set of threads 50 formed by the body 22. A boundary 58 separates the portions of the second set of threads 52. The exterior abutment surface 74 intersects the first set of threads 50 between most adjacent ones of the crest 54 and the root 56. The tip insert 70 may be formed of a radiolucent material, a radiopaque material, or a combination thereof without deviating from the scope of the present inventive concept. In the exemplary embodiment, the tip insert 70 is formed of a radiopaque material such as, but not limited to metal or the like. It is foreseen, however, that the tip insert 70 may be formed of a material having a modulus of elasticity that is the same as or substantially similar to that of cortical bone, such as, but not limited to thermoplastic polymer, e.g., polyether ether ketone (PEEK) without deviating from the scope of the present inventive concept.

A third component or head insert 90 includes an extension 92 that extends partially into the body 22 from an exterior abutment surface 94 of the head insert 90. The head insert 90 abuts the body 22 at the exterior abutment surface 94 and at an interior abutment surface 96, which is spaced from the exterior abutment surface 94 and forms an end of the extension 92 of the head insert 90. An aperture 98 partially extends along a length of the head insert 90 and receives a portion of the core 60 therein. An outermost portion 100 of the head insert 90 surrounds the receiver 44. The head insert 90 forms a portion of the second set of threads 52 with a remainder portion of the second set of threads 52 formed by the body 22. A boundary 104 separates the portions of the second set of threads 52. Interior portions 106, 108 of the head insert 90 are exposed through elongated receivers or notches 110, 112 in the second set of threads 52. The notches 110, 112 extend through a portion of the second set of threads 52. The head insert 90 may be formed of a radiolucent material, a radiopaque material, or a combination thereof without deviating from the scope of the present inventive concept. In the exemplary embodiment, the head insert 90 is formed of a radiopaque material such as, but not limited to metal or the like. It is foreseen, however, that the head insert 90 may be formed of a material having a modulus of elasticity that is the same as or substantially similar to that of cortical bone, such as, but not limited to thermoplastic polymer, e.g., polyether ether ketone (PEEK) without deviating from the scope of the present inventive concept.

Turning to FIG. 3, an X-ray image of multiple ones of the screw 20 of the present inventive concept are illustrated after implanting the screws 20 in a patient 118. As illustrated, the tip insert 70 and the head insert 90 of each of the screws 20 have enhanced visibility due to the radiopaque material forming the inserts 70, 90. Also, the body 22 and the core 60 are significantly less visible than the inserts 70, 90, and/or invisible, due to the radiolucent material forming the body 22 and the core 60. Accordingly, a surgeon using the screw 20 of the present inventive concept can readily identify outermost portions of the screw 20 with minimized distortion, thereby advantageously providing complete awareness of positioning and alignment of the screw 20.

Figure 4:
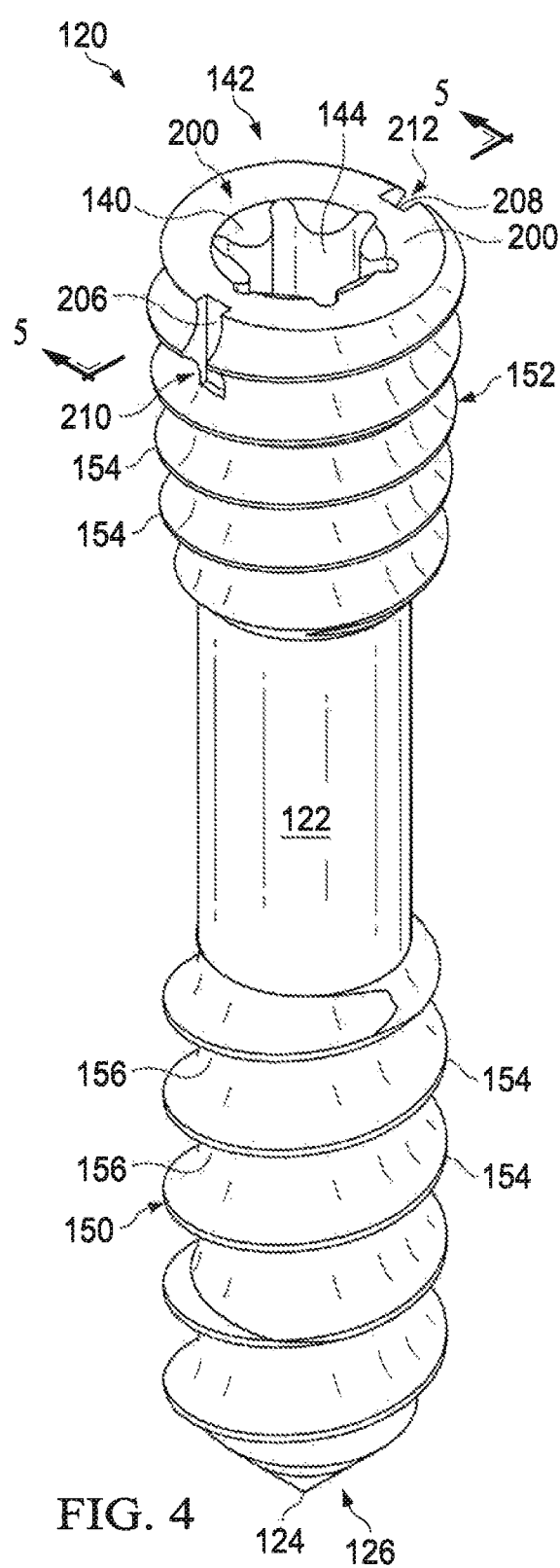
FIG. 4 is a perspective view of a hybrid radiolucent screw of the present inventive concept prior before implanting the screw in a patient by a surgeon during an orthopedic surgical procedure.
Figure 5:
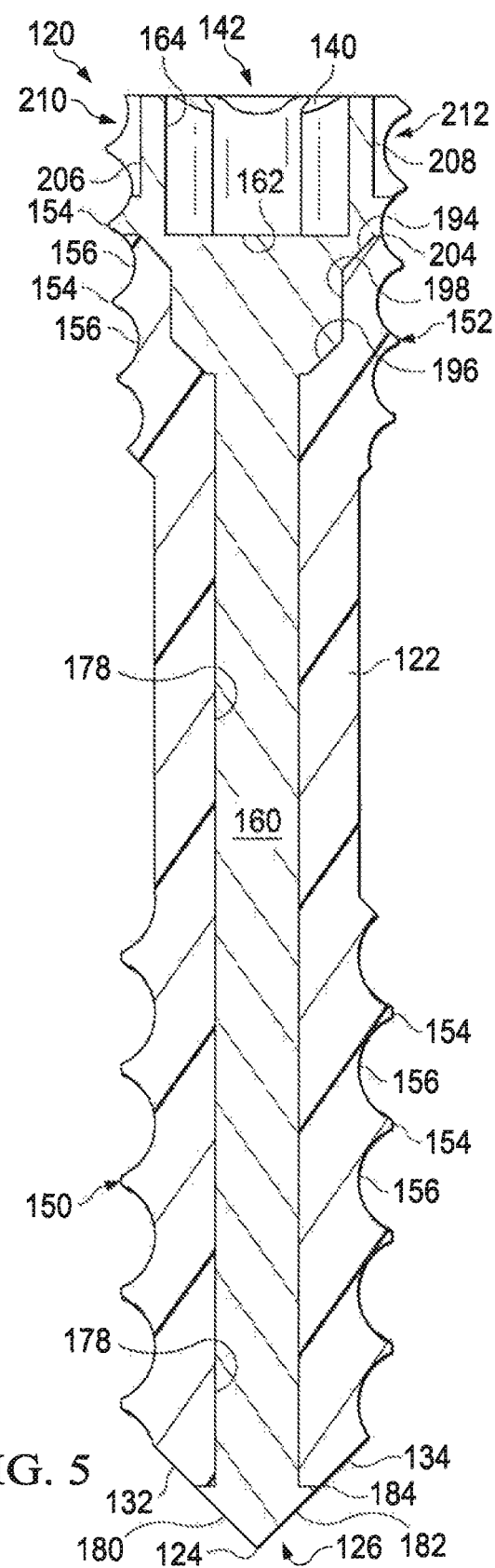
FIG. 5 is cross-section view of the screw of FIG. 4 taken along line 5-5 of FIG. 4.

Turning to FIGS. 4 and 5, a screw 120 of the present inventive concept is illustrated prior to use by a surgeon in the surgical procedure. The screw 120 includes an elongated body 122, which is formed along an elongated, central axis of the screw 120. The body 122 is formed of a radiolucent material with a modulus of elasticity that is the same as or substantially similar to that of cortical bone. In the exemplary embodiment, the body 122 is formed of a thermoplastic polymer such as polyether ether ketone (PEEK), but it is foreseen that the body 122 may be formed of another material with same or similar properties including, but not limited to the other radiolucent materials disclosed herein, without deviating from the scope of the present inventive concept.

The body 122 cooperatively defines an outermost surface of a first end 126 of the screw 120, which includes a tip 124, as further discussed hereafter. In the exemplary embodiment, the first end 126 includes angled sides 132, 134 of the body 122. It is foreseen, however, that the first end 126 of the screw 120 could include a plateau between angled sides 132, 134 without deviating from the scope of the present inventive concept.

The body 122 further includes a head 140, which defines an outermost surface of a second end 142 of the screw 120. In the exemplary embodiment, the head 140 includes a nested receiver 144 formed therein and extending partially into a centermost portion of the head 140 and along the central axis of the body 122.

The screw 120 further includes a first set of threads 150 and a second set of threads 152, which are spaced from each other along the body 122. The first set of threads 150 begin at the first end 126 and adjacent to the tip 124, and partially extend along the body 122. The second set of threads 152 begin and partially extend along the body 122 and terminate at the second end 142 and adjacent to the head 140. Each of the threads 150, 152 include a plurality of alternating crests 154 and roots 156, with sloped surfaces therebetween. The plurality of crests 154 define a major diameter of the threads 150, 152, the plurality of roots 156 define a minor diameter of the threads 150, 152, and each sloped surface of the sloped surfaces therebetween define a thread angle of the threads 150, 152.

A first component or core 160 extends entirely between the first end 126 and the second end 142, and along the central axis of the body 122. In the exemplary embodiment, an outermost portion of the core 160 forms a portion of the sides 132, 134 at the first end 126, and defines the receiver 144, i.e., forms an interior bottom surface 162 and interior side surface 164, at the second end 142 of the screw 120. In the exemplary embodiment, the core 160 has a first uniform diameter from the sides 132, 134 to a point adjacent to the receiver 144, at which point the diameter progressively increases and further extends along the central axis at a second uniform diameter that is larger than the first uniform diameter, and terminates to define an outermost portion of the second end 142. The core 160 may be formed of a radiolucent material, a radiopaque material, or a combination thereof without deviating from the scope of the present inventive concept. In the exemplary embodiment, the core 160 is formed of a radiopaque material such as, but not limited to metal or the like. It is foreseen, however, that the core 160 may be formed of a material having a modulus of elasticity that is the same as or substantially similar to that of cortical bone, such as, but not limited to thermoplastic polymer, e.g., polyether ether ketone (PEEK) and/or other radiolucent material including, but not limited to the other radiolucent materials disclosed herein, without deviating from the scope of the present inventive concept. It is also foreseen that the core 160 may be formed of a radiopaque material, such as one or more of the radiopaque materials disclosed herein, while the body 122 may be formed of a radiolucent material, such as one or more of the radiolucent materials disclosed herein, without deviating from the scope of the present inventive concept.

The tip 124 of the body 122 includes an aperture 178 extending along an entire length of the body 122 and the core 160 therethrough. In this manner, an outermost angled portion 180 of the core 160 and the angled side 132 of the body 122 collaboratively form a planar surface, and an outermost angled portion 182 of the core 160 and the angled side 134 of the body 122 form another planar surface. The planar surfaces of the body 122 and the core 160 collaboratively define the tip 124, which forms a portion of the first set of threads 150. A boundary 184 extends between the angled sides 132, 134 and the angled portions 180, 182.

The core 160 abuts the body 122 at an exterior abutment surface 194 of the body 122 and at an interior abutment surface 196 of the body 122. The surfaces 194, 196 are spaced from each other along the aperture 178 of the body 122. A portion 198 of the aperture 178 receives a portion of the core 160 therethrough. An outermost portion 200 of the core 160 surrounds the receiver 144. The core 160 forms a portion of the second set of threads 152 with a remainder portion of the second set of threads 152 formed by the body 122. A boundary 204 separates the portions of the second set of threads 152. Interior portions 206, 208 of the head 140 are exposed through elongated receivers or notches 210, 212 in the second set of threads 152. The notches 210, 212 extend through a portion of the second set of threads 152.

In this manner, the core 160 of the screw 120 has enhanced visibility in an X-ray image due to the radiopaque material forming the core 160. Further, the body 122 is significantly less visible than the core 160, or invisible, due to the radiolucent material forming the body 122. Accordingly, a surgeon using the screw 120 of the present inventive concept can readily identify outermost portions of the screw 120 with minimized distortion, thereby advantageously providing complete awareness of positioning and alignment of the screw 120.

Regarding manufacture of the screw 20 and the screw 120, steps are provided as follows, and exemplified with the screw 20, but are equally applicable to each of the screw 20 and the screw 120, as would become apparent to one of ordinary skill in the art through the description provided herein.

The screw 20 is manufactured by forming the body 22 having a portion of the first set of threads 50 and a portion of the second set of threads 52. Next, the core 60 is extended into the body 22. Next, the tip insert 70, which includes another portion of the first set of threads 50, is secured to the core 60, via bonding or the like, so that the tip insert 70 abuts the body 22. In this manner, the core 60 and the tip insert 70 collaboratively form the tip 24 of the screw 20. Next, the head insert 90, which includes another portion of the second set of threads 52, is secured to the core 60, via bonding or the like, so that the head insert 90 abuts to the body 22. In this manner, the head insert 90 and the receiver 44 collaboratively form the head 40 of the screw 20.

Having now described the features, discoveries and principles of the general inventive concept, the manner in which the general inventive concept is constructed and used, the characteristics of the construction, and advantageous, new and useful results obtained; the new and useful structures, devices, tools, elements, arrangements, parts and combinations, are set forth in the appended claims.

It is also to be understood that the following claims are intended to cover all of the generic and specific features of the general inventive concept herein described, and all statements of the scope of the general inventive concept which, as a matter of language, might be said to fall there between.

What is claimed is:

1. A screw comprising:
an elongated body defining a central axis of the screw, the body having a first end and a second end portion, the second end portion defining a first set of threads;
a tip insert secured to the first end of the body, the tip extending along a portion of the body; and
a head insert secured to the second end portion of the body, the head insert defining a second set of threads, abutting the second end portion of the body such that the first set of threads are continuous with the second set of threads, and having a central receiver.

2. The screw according to claim 1,
wherein,
the tip insert is operable to function as a radiopaque marker.

3. The screw according to claim 2,
wherein,
the tip insert includes an interior abutment surface spaced from an exterior abutment surface.

4. The screw according to claim 1, further comprising:
a set of threads defined by the tip insert and the body.

5. The screw according to claim 1,
wherein,
the head insert includes an interior abutment surface and an exterior abutment surface.

6. The screw according to claim 1, further comprising:
a set of threads defined by the body and the head insert.

7. The screw according to claim 1, further comprising:
an elongated receiver (i) formed in a set of threads, and (ii) exposing at least a portion of the head insert.

8. The screw according to claim 1, further comprising:
a core extending along the body,
wherein,
the body is formed of a radiolucent material,
the core is formed of a radiopaque material or the radiolucent material, and
the tip insert and the head insert are formed of the radiopaque material or the radiolucent material.

9. The screw according to claim 1,
wherein,
only a portion of the tip is formed of polyether ether ketone.

10. The screw according to claim 1,
wherein,
the central receiver is nested within the head insert, includes a bottom surface, and exposes an interior portion of the head insert.

11. The screw according to claim 1, further comprising:
a core extending along an interior of the body, the head insert, and the tip insert.

12. A screw comprising:
an elongated body;
a tip defining a first end of the body and including a tip portion of a core and a tip insert;
a head insert defining a second end of the body and including a head portion of the core, the head insert having a central receiver;
a first set of threads at least partially defined by the tip; and
a second set of threads at least partially defined by the head insert,
wherein,
the tip insert extends beyond the first set of threads and abuts an interior surface of the body.

13. The screw according to claim 12,
wherein,
the head insert abuts the body along the second set of threads.

14. A method of manufacturing a hybrid screw, the method comprising the steps of:
forming an elongated radiolucent body defining at least a portion of a set of threads;
extending a core into the body;
securing a first radiopaque component to the core, the core and the first radiopaque component forming a tip of the screw; and
securing a second radiopaque component to the core, the body and the second radiopaque component forming at least a portion of a head of the screw.

15. The method according to claim 14,
the first radiopaque component includes an interior abutment surface spaced from an exterior abutment surface.

16. The method according to claim 15,
wherein,
the first radiopaque component abuts an interior surface of the body along the set of threads and within outermost perimeters of the set of threads.

17. The method according to claim 14,
wherein,
the set of threads is defined by the first radiopaque component and the body.

18. The method according to claim 14,
wherein,
the head is defined by the core, the body, and the second radiopaque component.

19. The method according to claim 14, wherein,
   the second radiopaque component abuts the body along the set of threads.

\* \* \* \* \*